US010448961B2

(12) United States Patent
Preiss et al.

(10) Patent No.: US 10,448,961 B2
(45) Date of Patent: Oct. 22, 2019

(54) APPARATUS AND METHOD FOR FRAGMENTING AND ASPIRATING MATERIALS FROM A BODY LUMEN

(71) Applicant: LUMENIS LTD., Yokneam (IL)

(72) Inventors: Assaf Preiss, Shimshit (IL); Moshe Elazar, Kadima-Tzoran (IL); Alon Shacham, Katzir (IL)

(73) Assignee: LUMENIS LTD. (IL)

( * ) Notice: Subject to any disclaimer, the term of this patent is extended or adjusted under 35 U.S.C. 154(b) by 43 days.

(21) Appl. No.: 15/904,341

(22) Filed: Feb. 24, 2018

(65) Prior Publication Data

US 2018/0271545 A1    Sep. 27, 2018

Related U.S. Application Data

(62) Division of application No. 14/595,312, filed on Jan. 13, 2015.

(60) Provisional application No. 61/927,426, filed on Jan. 14, 2014.

(51) Int. Cl.

| A61B 17/22 | (2006.01) |
|---|---|
| A61B 17/34 | (2006.01) |
| A61B 18/26 | (2006.01) |
| A61B 18/00 | (2006.01) |

(52) U.S. Cl.
CPC .......... *A61B 17/22* (2013.01); *A61B 17/3421* (2013.01); *A61B 18/26* (2013.01); *A61B 2017/3445* (2013.01); *A61B 2017/3447* (2013.01); *A61B 2018/00511* (2013.01); *A61B 2018/00517* (2013.01); *A61B 2218/002* (2013.01); *A61B 2218/007* (2013.01)

(58) Field of Classification Search
CPC ..... A61B 17/22; A61B 17/3421; A61B 18/26; A61B 2017/3445; A61B 2017/3447; A61B 2018/00511; A61B 2018/00517; A61B 2218/002; A61B 2218/007; A61B 18/20–18/28
See application file for complete search history.

(56) References Cited

U.S. PATENT DOCUMENTS

| 4,894,057 | A | 1/1990 | Howes |
|---|---|---|---|
| 5,429,596 | A | 7/1995 | Arias |
| 6,440,123 | B1 | 8/2002 | Engel |
| 2003/0125719 | A1 | 7/2003 | Furnish |
| 2004/0076377 | A1 | 4/2004 | Mizukami |
| 2004/0238098 | A1 | 12/2004 | Bleckmann |
| 2005/0203497 | A1 | 9/2005 | Speeg |
| 2006/0235269 | A1 | 10/2006 | Waxman |
| 2007/0293726 | A1 | 12/2007 | Goldfarb |
| 2009/0018531 | A1 | 1/2009 | Welches |
| 2011/0144630 | A1 | 6/2011 | Loeb |
| 2012/0029354 | A1 | 2/2012 | Mark |

*Primary Examiner* — Gary Jackson
*Assistant Examiner* — Jonathan Kuo
(74) *Attorney, Agent, or Firm* — ISUS Intellectual Property PLLC

(57) ABSTRACT

A device for insertion into a body lumen includes an operator unit which may be hand held by an operator. A cannula is operatively associated with the operator unit and the cannula includes two parallel lumens. At least one of two lumens terminates at its distal end before the distal end of the other lumen and wherein one of the two lumens is contained at most partially within the other lumen.

3 Claims, 15 Drawing Sheets

PERSPECTIVE VIEW

PRESPECTIVE VIEW

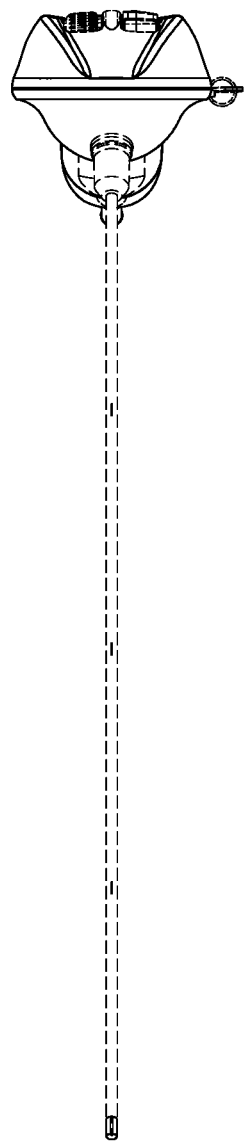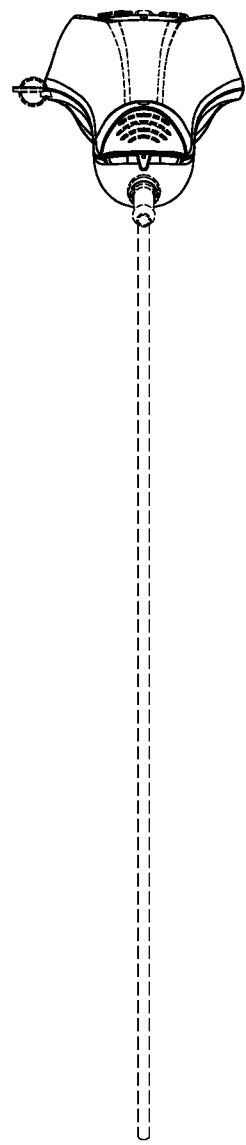
FIG.10C
FRONT VIEW
FIG.10D
REAR VIEW

SIDE VIEW

SIDE VIEW

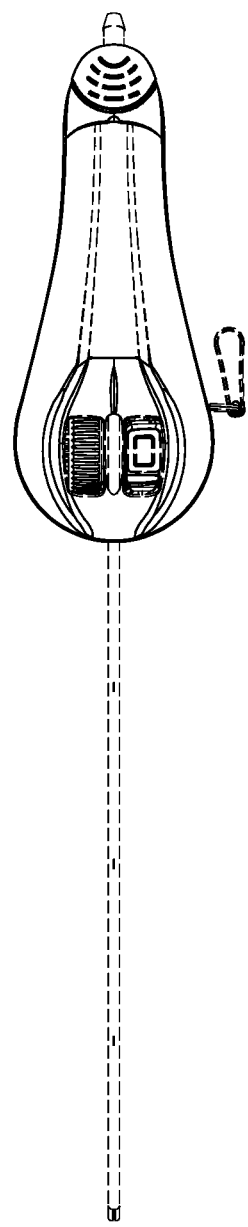
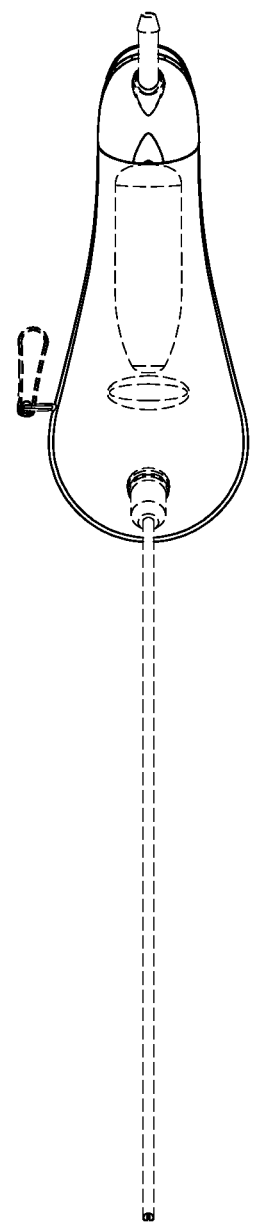
FIG.10G
TOP VIEW
FIG.10H
BOTTOM VIEW

APPARATUS AND METHOD FOR FRAGMENTING AND ASPIRATING MATERIALS FROM A BODY LUMEN

RELATED APPLICATIONS

This application is a divisional application of U.S. application Ser. No. 14/595,312, filed Jan. 13, 2015, which is related to and claims priority to U.S. Provisional Application No. 61/927,426, filed Jan. 14, 2014, the entirety of which is herein incorporated by reference.

FIELD OF THE INVENTION

This invention relates to medical devices and in particular to devices which are adapted to fragment materials contained within a body lumen, including urinary tract stones, bladder stones, kidney stones and the like, using optical energy, especially lasers, and removing fragmented materials from the body lumen.

BACKGROUND

Medical devices which are used to fragment and remove stones and other materials from, for example, the urinary tract, the bladder and the kidneys (hereinafter referred to as "stones"), are known in the art. An example of such a device is shown in U.S. Pat. No. 6,517,531. In this patent, a dual lumen elongated member is used, respectively, for the purposes of providing a first lumen for an optical fiber and a second lumen to aspirate fragmented stones or other materials.

One of the problems associated with the foregoing patent as well as other prior art is that a balance must be struck between the overall size or diameter of the device to be introduced into the urinary tract of a human being and to fit the working channel of an urethascope. The size should preferably be chosen not only so that it will fit within the space constraints above but also be of a size to be able to incorporate an aspiration lumen as well as a lumen to contain an optical fiber which is used to break apart, in this example, stones or other materials in urinary tract. As can be seen, FIG. 1 represents the prior art and it can be seen that the optical fiber lumen is contained within the aspiration lumen. This arrangement, of course, decreases the size of the aspiration lumen and limits the size of the degree of the stones or other fragmented materials which can be suctioned through the aspiration lumen to outside the body. Both FIGS. 1A and 1B show two variations of prior art systems which include the optical fiber lumen within the aspiration lumen. Thus, there is a need for a two lumen device which maintains the maximum size of the aspiration lumen so that larger pieces of fragmented stones or other materials may be aspirated while still containing sufficient space for the optical fiber lumen.

Another problem associated with dual lumen devices of the type of the present invention is that, as can be seen in prior art FIGS. 1A and 1B, the fiber lumen and the aspiration lumen terminate at the same plane. This results in the inability of the physician or other operator to visualize the optical fiber tip unless it is pushed out of the optical lumen. In a known procedure, in addition to the use of the device such as is described in the above patent and in the present invention an additional device named a urethascope is positioned in the body lumen and provides, among other things, a visualization lumen to the physician to visualize the materials sought to be removed and to guide the optical fiber.

It is also known that during the process and procedure of fragmenting stones and other materials that the tip of the optical fiber may itself fragment due to the intense energy delivered through and at the tip of the optical fiber. Because the optical fiber lumen and the plane of the aspiration lumen terminate at the same plane, it is often difficult for the physician to inspect the tip of the optical fiber. Thus, what is needed is a dual lumen device which allows for easy visualization of the optical fiber tip.

Another issue associated with such devices described in the above patent and the present invention is the control of the optical fiber into the body cavity and its advancement within the body cavity to stones or other materials which are sought to be fragmented. Thus, what is needed is a simple and accurate means to move and control the position of the optical fiber and its tip in the urinary tract to better be able to aim the optical fiber tip at the stones to be fragmented.

Yet another issue associated with such devices is the ability to provide a handpiece that is easily gripped and manipulated by the operator of the device in use and which provides all controls for various functions, such as advancement of the optical fiber at gross movement levels and fine movement levels and control over the function of aspiration and irrigation within easy reach of the operator during a procedure.

SUMMARY OF THE INVENTION

In an aspect, a device for insertion into a body lumen includes an operator unit adapted to be held by an operator; a cannula operatively associated with the operator unit. The cannula includes at least two parallel lumens. At least one of the at least two lumens terminates at its distal end before the distal end of the other of the at least two lumens.

In another aspect, the at least one lumen which terminates before the distal end of the other of the at least two lumens is contained at most partially within the at least one other lumen which extends beyond the distal end of the at least one lumen which terminates before the distal end of the at least two lumens.

In yet another aspect, a device for insertion into a body lumen includes an operator unit adapted to be held by an operator; a cannula operatively associated with the operator unit. The cannula includes at least two parallel lumens. The at least two lumens is contained at most partially within the at least one other lumen.

In a further aspect, the cannula is operatively associated with the operator unit at the proximal end of the cannula.

In yet another aspect, one of the at least two parallel lumens is adapted for receiving an optical fiber and the other of the at least two parallel lumens is adapted for one or more of aspiration and irrigation of materials within the body lumen.

In yet a further aspect, the operator unit includes one or more controls to manipulate one or more of the optical fiber and the one or more of the aspiration and irrigation of materials within the body lumen.

In yet a further aspect, the at least one lumen terminating before the distal end of the other of the at least two lumens is wholly outside of the other of the at least two lumens.

In an aspect, the control to manipulate the optical fiber includes a wheel operatively associated with the operator unit which one of directly or indirectly engages the optical fiber to advance the optical fiber within the operator unit. Furthermore, at least two rollers are operatively connected with the wheel, the at least two rollers being engageable with the optical fiber therebetween and wherein movement of the wheel causes the optical fiber to move due to contact with the moving at least two rollers. At least one of the at least two rollers is of a resilient material.

In another aspect, the control to manipulate the optical fiber includes a mechanism to disengage the wheel from the optical fiber such that the operator may manually advance the optical fiber.

In yet another aspect, the one or more controls for one or more of aspiration and irrigation of materials includes a mechanical switch and a flexible tube operatively associated with the mechanical switch, wherein the mechanical switch, when depressed, engages and at least partially collapses the flexible tube to stop one of: aspiration or irrigation of materials in the body lumen.

In a further aspect, the mechanism includes a tube for containing the optical fiber, and wherein the tube is movable from a first position to a second position, in the second position being interposed between the at least two rollers such that an optical fiber within the tube is not engaged with the at least two rollers and may be advanced by the operator without movement of the wheel.

BRIEF DESCRIPTION OF THE DRAWINGS

FIGS. 10A to 10H illustrate the overall design of the handpiece.

DETAILED DESCRIPTION

Figure 2:
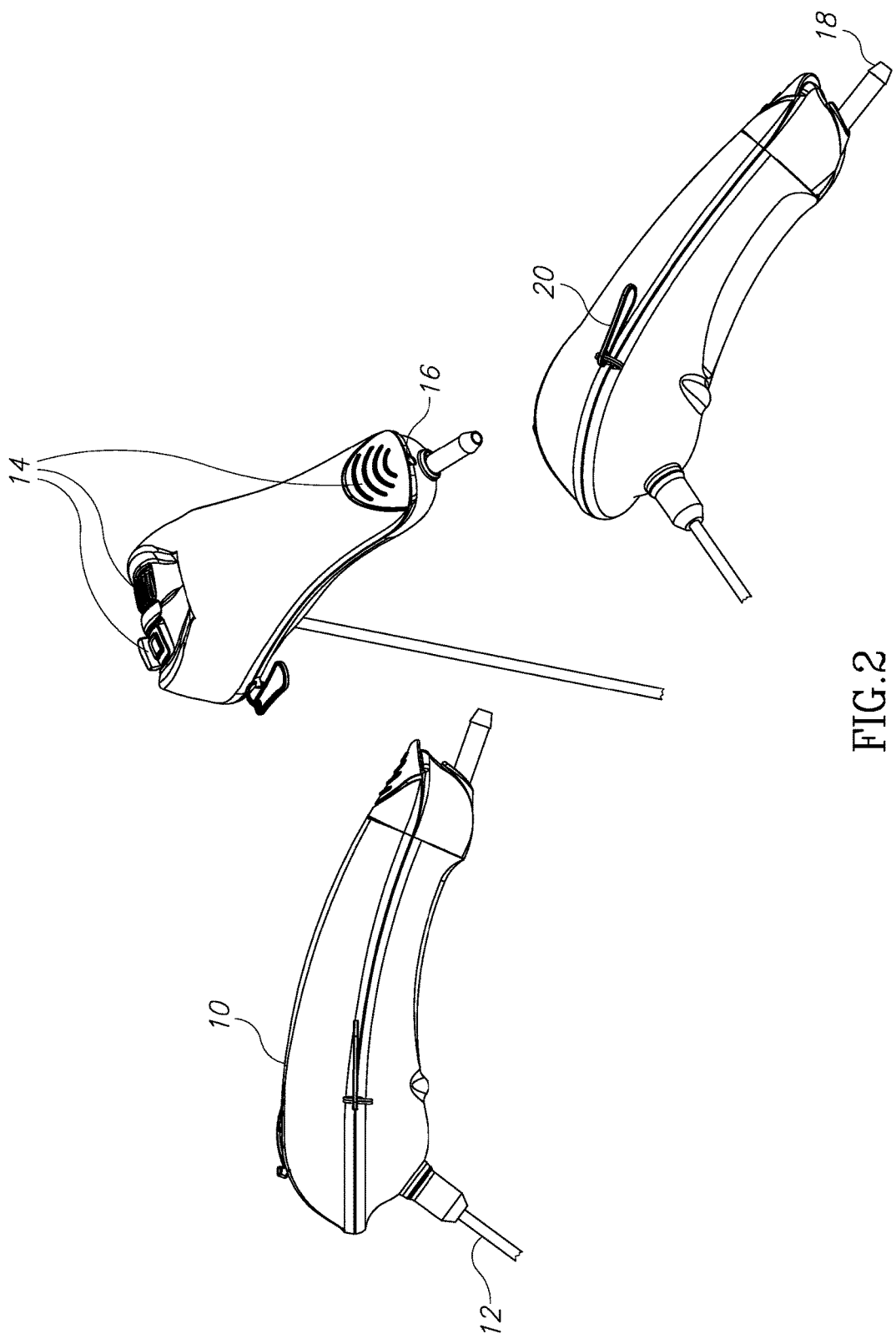
FIG. 2 illustrates overall views of the apparatus of the present invention.

Turning now to FIG. 2, this figure illustrates the overall structure of the device of the present invention. This can be seen as a handpiece 10, which will be described in greater detail below, having a cannula 12 with at least two lumens, the first lumen for the aspiration and irrigation of materials and the second a lumen for containing and guiding an optical fiber. The handpiece 10 also contains controls 14 as seen in FIG. 2 and as will be described below in detail in reference to FIGS. 7 to 9 below, to control the aspiration/irrigating means as well as the advancement of the optical fiber. Thus, in FIG. 2, the proximal end of the handpiece 10 includes an optical fiber port 16 and a vacuum port 18, to be described below. In addition, a removable pin 20 is included to control the release of the mechanical vacuum switch, to be described below.

The cannula 12 may be constructed of any number of materials including metal. While the cannula 12 is shown as being more or less orthogonal to the handpiece 10, it is feasible to orient the angle between the handpiece 10 and the cannula 12 in any desired angle. The shape of the handpiece is ergonomically designed to allow easy handling and operation of the handpiece during a procedure. FIGS. 10A through 10H provide additional various views of the handpiece 10.

Figure 3:
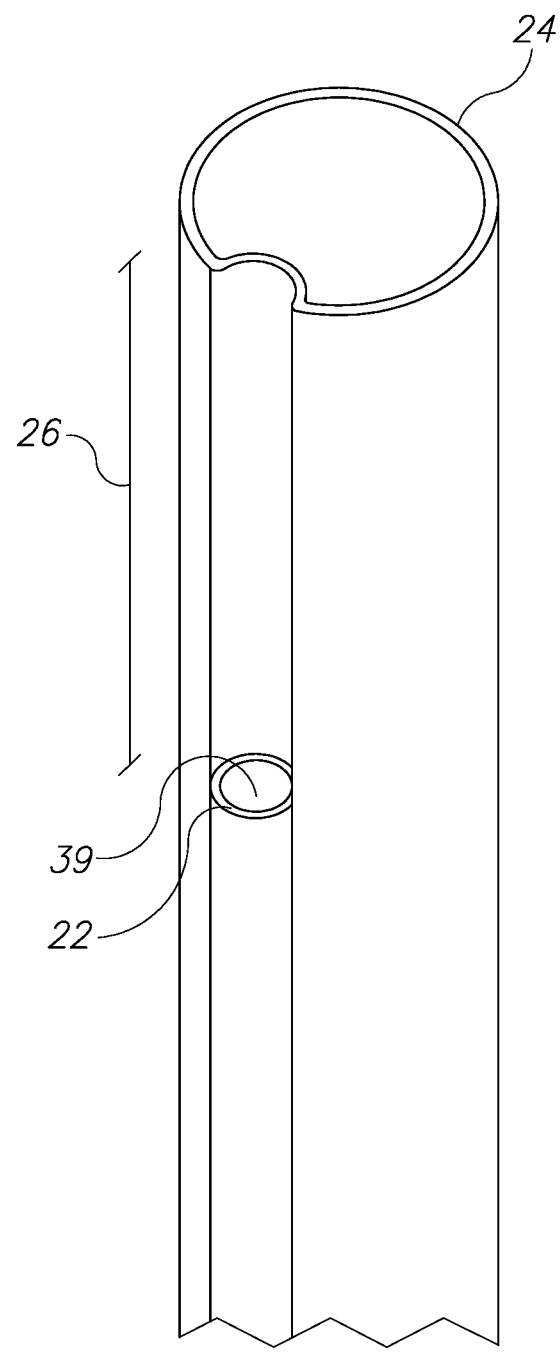
FIG. 3 illustrates the distal portion of a dual lumen elongated device of the present invention.
Figure 4B:
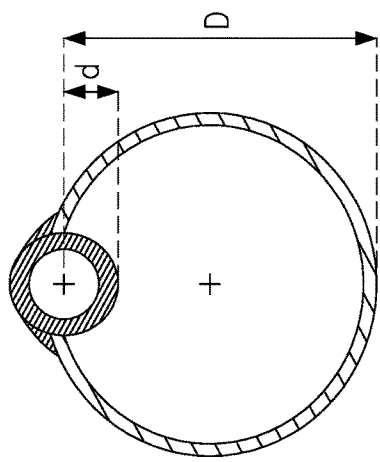
FIGS. 4A to 4C illustrate other embodiments of the device illustrated in FIG. 3.
Figure 4D:
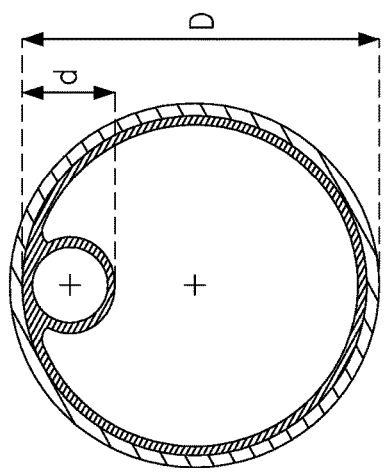
FIG. 4D illustrates another view of a prior art device.
Figure 4A:
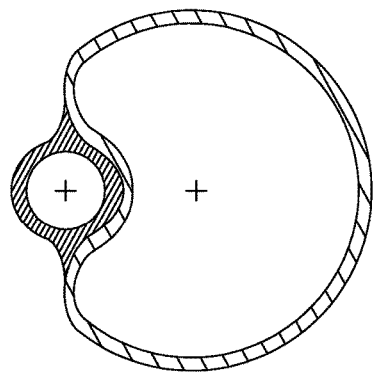
Figure 4C:
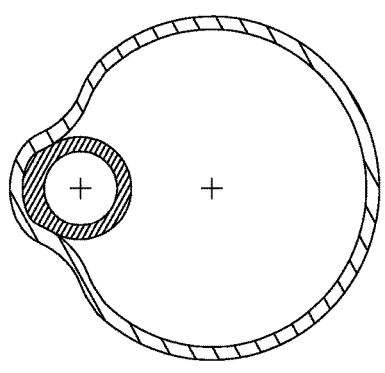

Turning now to FIG. 3, that figure illustrates another aspect of the present invention. As can be seen in FIG. 3, the distal end of the cannula 12 includes the distal end of the optical fiber lumen 22 as well as the distal end 24 of the aspiration/irrigation lumen. It is noted that the cannula which encompasses both the fiber lumen and the aspiration/irrigation lumen may be made of a metal material or any other suitable material such as a polymeric material and may be translucent or even transparent depending on the use to which it will be put. It can be seen in FIG. 3 that the distal end of the optical fiber lumen is not in the same plane as the distal end of the aspiration and irrigation lumen 24. The distal end of the optical fiber lumen is set back from the plane of the distal end of the aspiration and irrigation lumen by a distance 26 and this is for the purpose of allowing better visualization by the operator of the distal tip of the optical fiber than would be feasible if the distal tip of the optical fiber lumen 22 terminated on the same plane as the aspiration/irrigation lumen 24. The fiber tip and its jacket are very much visible to the physician during a procedure due to the "set back" of the optical fiber lumen, so that the position of the fiber tip and the condition of the fiber tip are readily viewable. Turning now to FIGS. 4A to 4C, these figures illustrate a number of alternative embodiments of the relationship between the optical fiber lumen and the aspiration/irrigation lumen. FIG. 4D represents the prior art discussed above in reference to FIGS. 1(*a*) and 1(*b*).

Figure 1A:
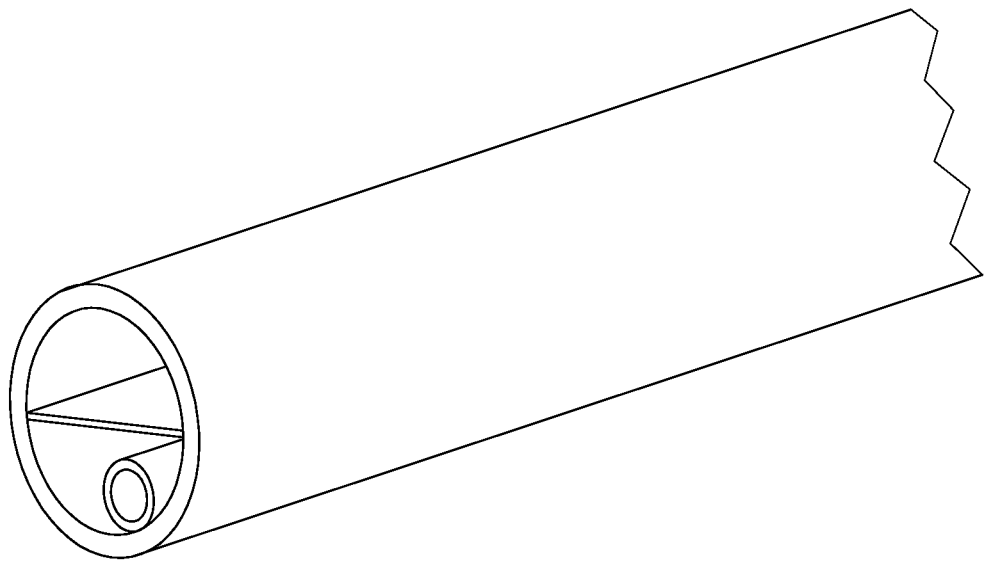
FIGS. 1A and 1B illustrate prior art dual lumen apparatuses.
Figure 1B:
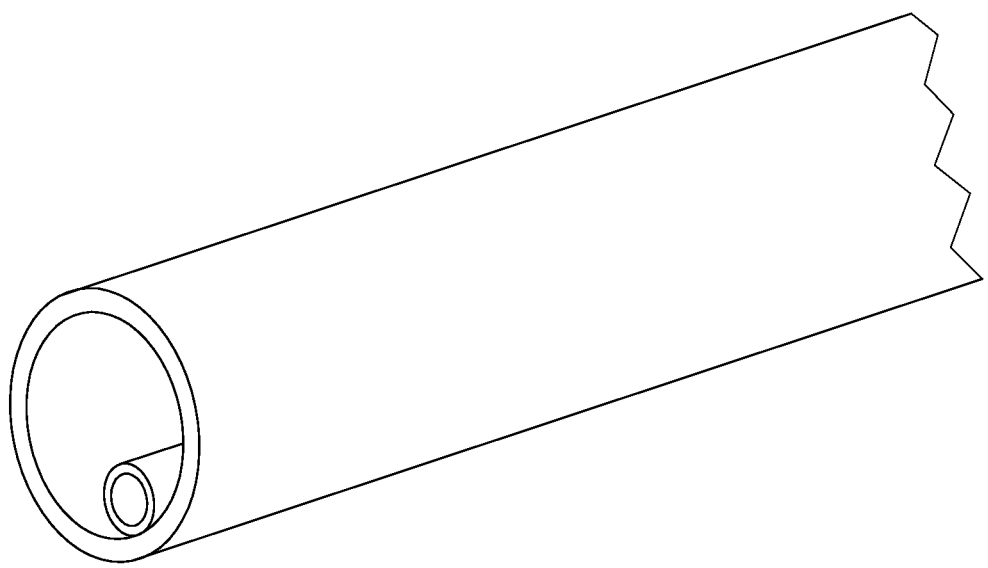

FIG. 4D illustrates the relationship between the optical fiber lumen and the aspiration and irrigation lumen as seen in the prior art devices of FIGS. 1A and 1B. In this embodiment, the optical fiber lumen is shown as being contained wholly within the aspiration/irrigation lumen. This results in a reduction in the maximum size of stones and other materials which may be aspirated through that lumen. For example, in the structure of the devices of prior art FIGS. 1A, 1B and 1D, if D is in diameter of the aspiration/irrigation lumen and d is the diameter of the optical fiber lumen, then the maximum stone or other material size which can be evacuated is D−d. However, in the devices illustrated in FIGS. 4A to 4C, the maximum stone or other material size which can be evacuated is D−½d, thus allowing the aspiration of larger stones and other materials while maintaining the same overall diameter of the combined lumens as in the prior art devices.

Figure 5:
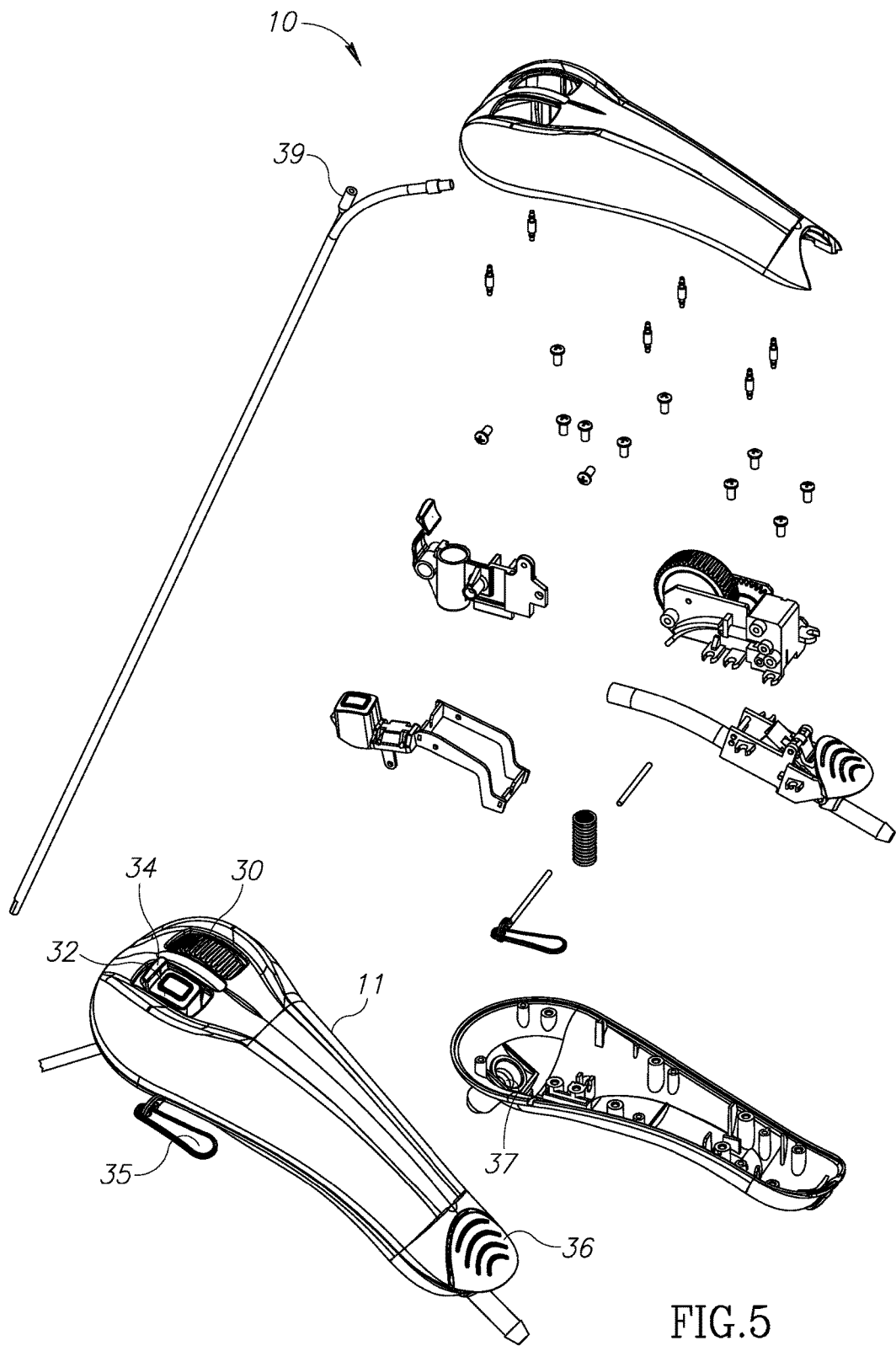
FIG. 5 illustrates an exploded view of the handpiece of the present invention.

FIG. 5 illustrates the handpiece 10 of FIG. 2 viewed from a perspective exploded view. The top section 11 of the handpiece 10 includes a wheel or roller control 30 which controls the advancement of the optical fiber. It also includes a mechanical switch 32 which controls the opening and the closing of the aspiration/irrigation lumen. It further includes a locking switch 34 which may be used to lock the aspiration/irrigation lumen in either an open or closed position to free the physician's fingers for other operations, such as manipulating the optical fiber to the vicinity of the stones or other materials which are thought to be fragmented by the optical fiber energy. Finally, a locking pin 35 is operatively connected to the mechanical switch to prevent activation of operation of the aspiration/vacuum function. A second optical fiber handling mechanism 36, as can be seen in FIG. 5 as 210 in FIG. 9, on the proximal portion of the handpiece provides further controls over the optical fiber advancement.

Figure 6:
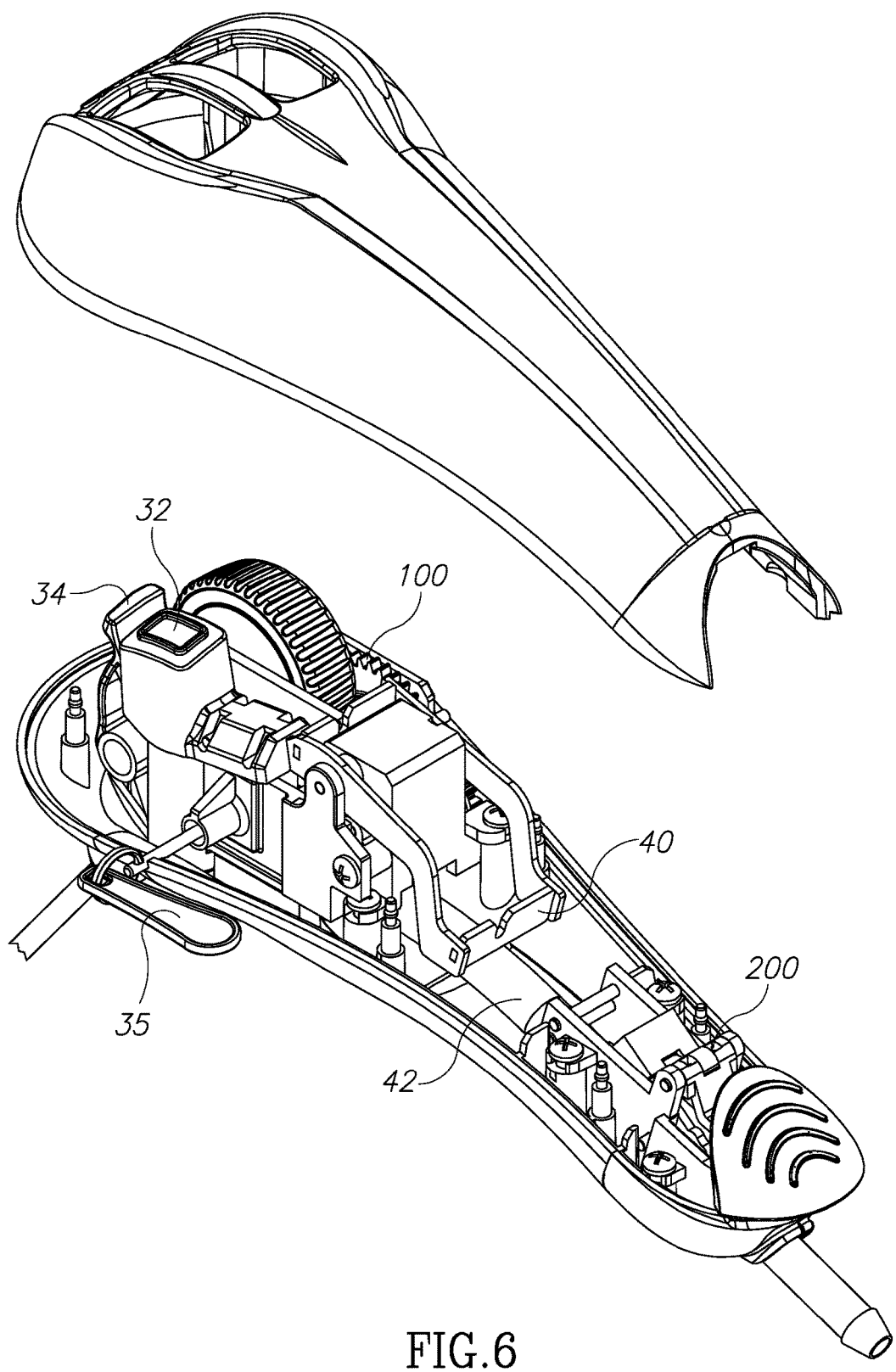
FIGS. 6 and 7 illustrate the handpiece and the contained mechanisms for advancing an optical fiber and controlling an aspiration/irrigating apparatuses.
Figure 7:
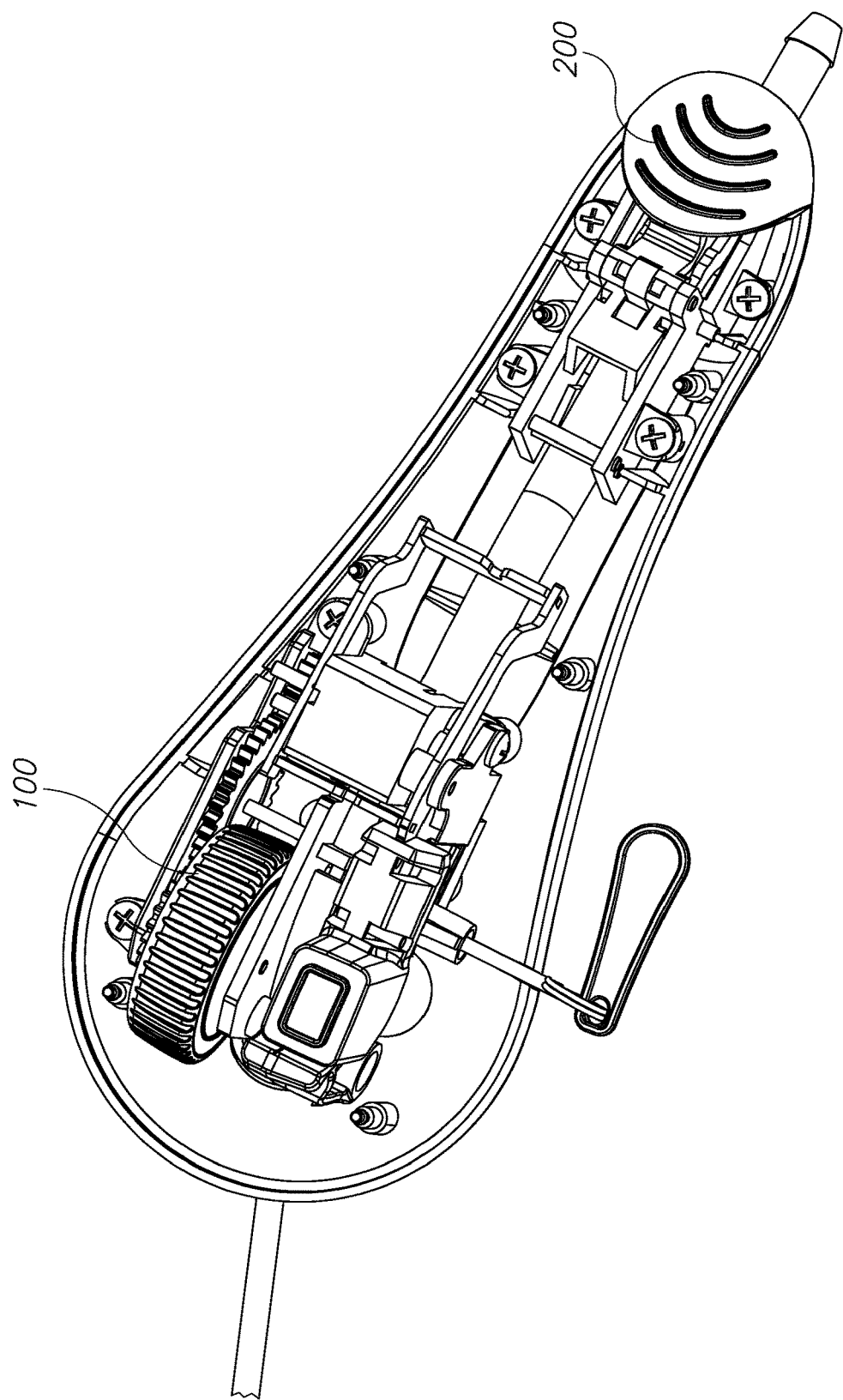
Figure 8A:
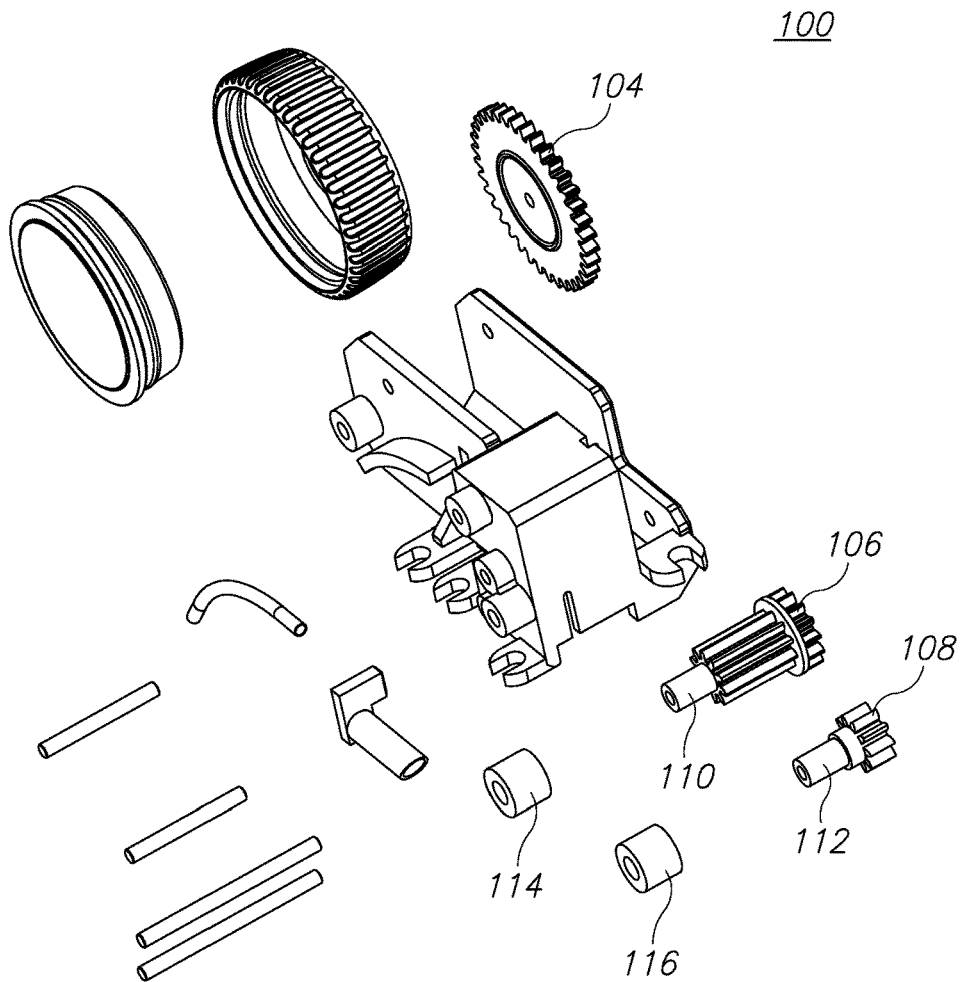
FIGS. 8A, 8B, 9A and 9B illustrate two of the devices for controlling the insertion and advancement of an optical fiber into the optical fiber lumen.

FIGS. 6 and 7 illustrate different views of the mechanisms to which the controls 30, 32, 34 and 36 are connected. The mechanical switch 32 may have a stopper 40 which presses onto a silicone or other material flexible aspiration/irrigation tube 42 so that the aspiration/irrigation tube 42 may be in either a normally collapsed/closed position or moved to an open position. The lock mechanism 34 may be used to keep the aspiration/irrigation channel in an open position, the default position being the position in which the stopper 40 presses against the tube to keep it closed. The locking switch 34 may be designed in any number of desired default orientations: always off so that no vacuum is in operation unless actuated; always on so that the vacuum is always on unless the operator disengages the operation; and a mode in which the vacuum is turned on any time the laser is activated so that aspiration occurs while fragmenting stones. The locking pin 35 when inserted into handpiece, interacts with the mechanical switch 32 to either prevent its depression and the depression of the stopper 40 or to hold the stopper 40 against the tube 42 to prevent actuation of the vacuum/aspiration function. In order to use the mechanical switch 32, the locking pin must be removed. FIGS. 7 and 8 show the device 100 (or button 30 in FIG. 5) positioned distally of the device 200 (or 36 in FIG. 5). As will be detailed below, each of these devices accepts and is capable of advancing (or retracting for that matter) an optical fiber that is inserted in the proximal portion of the handpiece in the vicinity of the vacuum fitting 18 shown in FIG. 2 as well.

Now to be discussed is the operation and structure of the mechanisms 100 and 200 which are utilized to control and advance the position of the optical fiber. Turning now to FIG. 8, that figure shows the "main" mechanism for controlling and advancing an optical fiber controlled more or less precisely by the wheel or roller 102. As can be seen the wheel or roller 102 is attached to a geartrain 104, 106 and 108 and that turning of the wheel or roller 102 will in turn cause rotation of shafts 110 and 112. Shafts 110 and 112 have mounted on them two rollers 114 and 116. There may be made of a resilient material and are spaced a distance that is slightly apart but sufficiently close that an optical fiber placed therebetween is constrained against movement or is moveable by rotation of the wheel or roller 102 and through geartrain 106 and 108. Distally of the rollers 114 and 116 is a curved tube 120. The tube 120 receives an optical fiber that has passed through the rollers 114 and 116. The distal end of the tube 120 is connected to or at least in the vicinity of opening 37 (best shown in FIG. 5). Thus, an optical fiber advanced through the device 100 under action of the wheel or roller 102 will exit the distal end of tube 120 and enter the lumen 39 which constitutes the fiber lumen as shown in FIGS. 3 and 5.

Figure 9A:
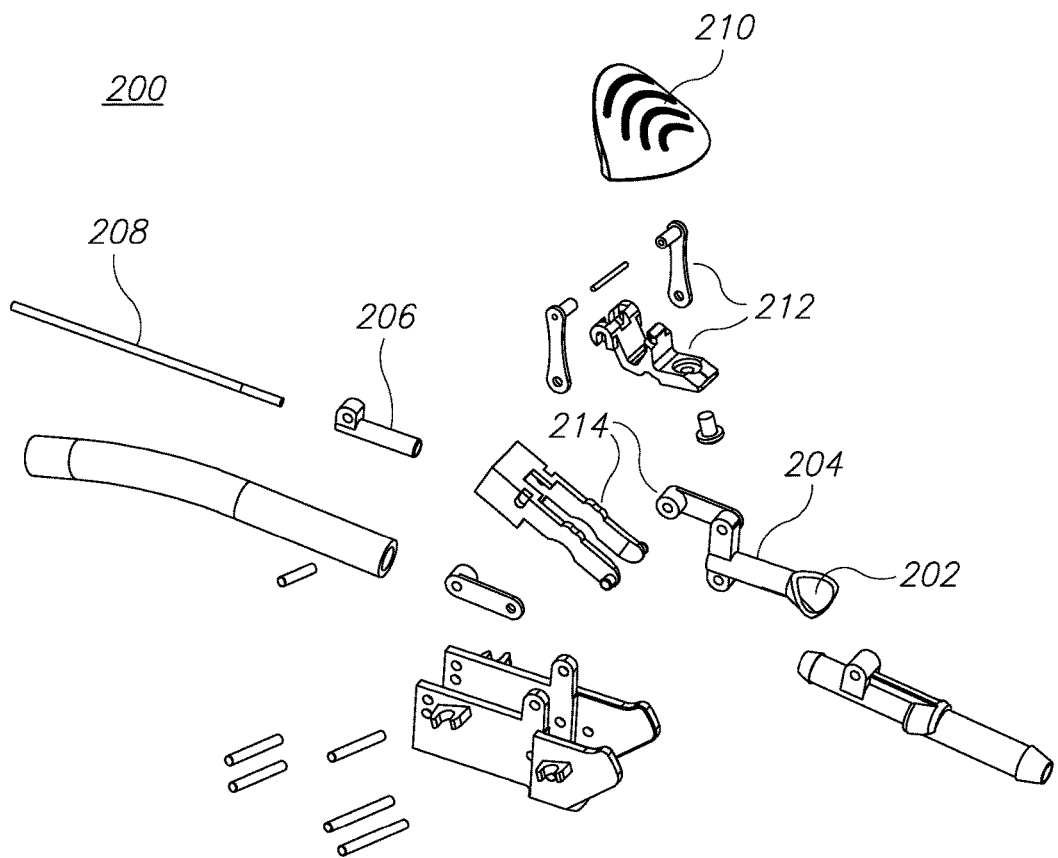

Turning now to FIG. 9, that figure illustrates the assembly 200 assembled towards the proximal portion of the handpiece 10 as may be seen in FIG. 6. An entry port 202 best seen in the exploded view of FIG. 9A includes a tube section 204. That section is further connected to tubes 206 and 208. An optical fiber inserted through the entry port 202 is advanced through tubes 204, 206 and 208 and will exit the distal end of tube 208 and enter, upon its advancement, into an entry port of the assembly 100 discussed above, then through the assembly to enter between rollers 114 and 116. AS described above, rotation of the wheel or roller 102 will advance the fiber through tube 120 and finally into fiber lumen 39 as seen in FIG. 5. Due to the geartrain, very precise movements of the advancing optical fiber may be made. However, when the optical fiber is first "loaded" into the entry port 202, to save time a more "gross" movement of the fiber through the handpiece and then through the fiber lumen may be desirable. This is achieved by the assembly 200 of FIG. 9. Assembly 200 includes an actuatable button 210 which is operatively connected to the lever train 212 and 214 such that lifting upward the button 210 results in the tube 208 moving in the distal direction towards the assembly 100. Such distal movement causes tube 208 to enter between rollers 114 and 116. Once this is accomplished, the rollers 114 and 116 will be in contact with the outer surface of the tube 208. As a consequence, an optical fiber will be able to be "pushed" through the assembly 100 and the assembly 200 and through the fiber lumen 39 so that the operator may began the procedure. After such advancement, the operator may push the button down, which cause withdrawal in a proximal direction of the tube 208 so that the rollers 114 and 116 contact the optical fiber, thus assuring advancement by way of the wheel or roller 102.

Figure 8B:
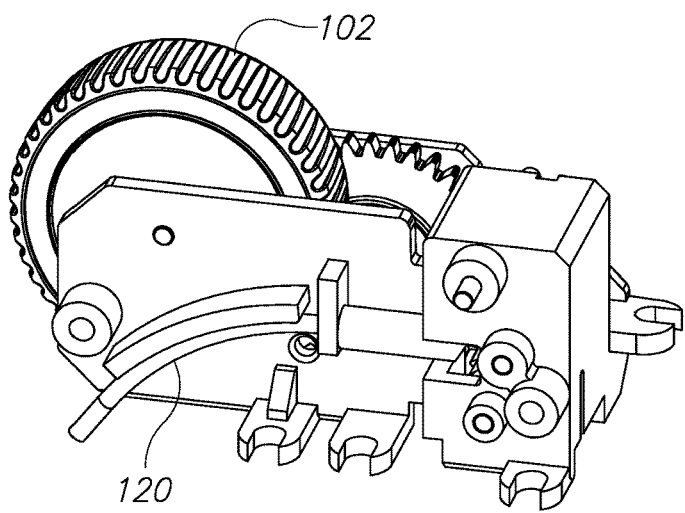
Figure 9B:
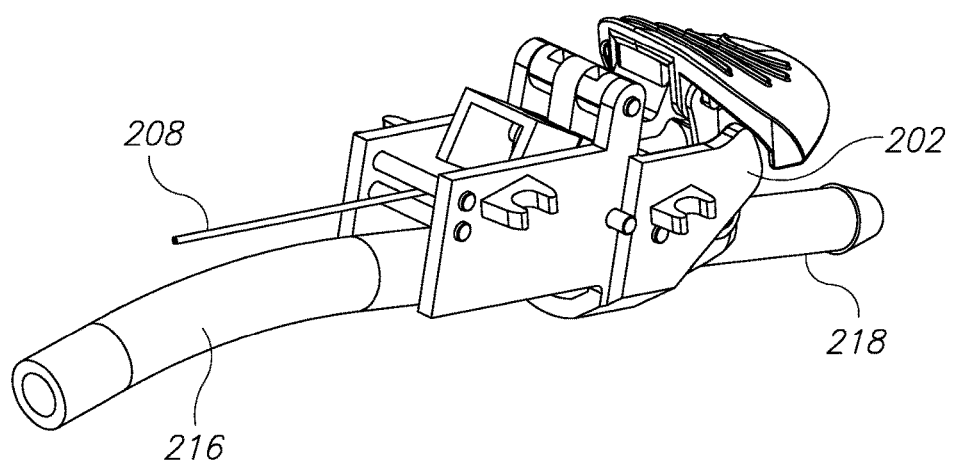
Figure 10A:
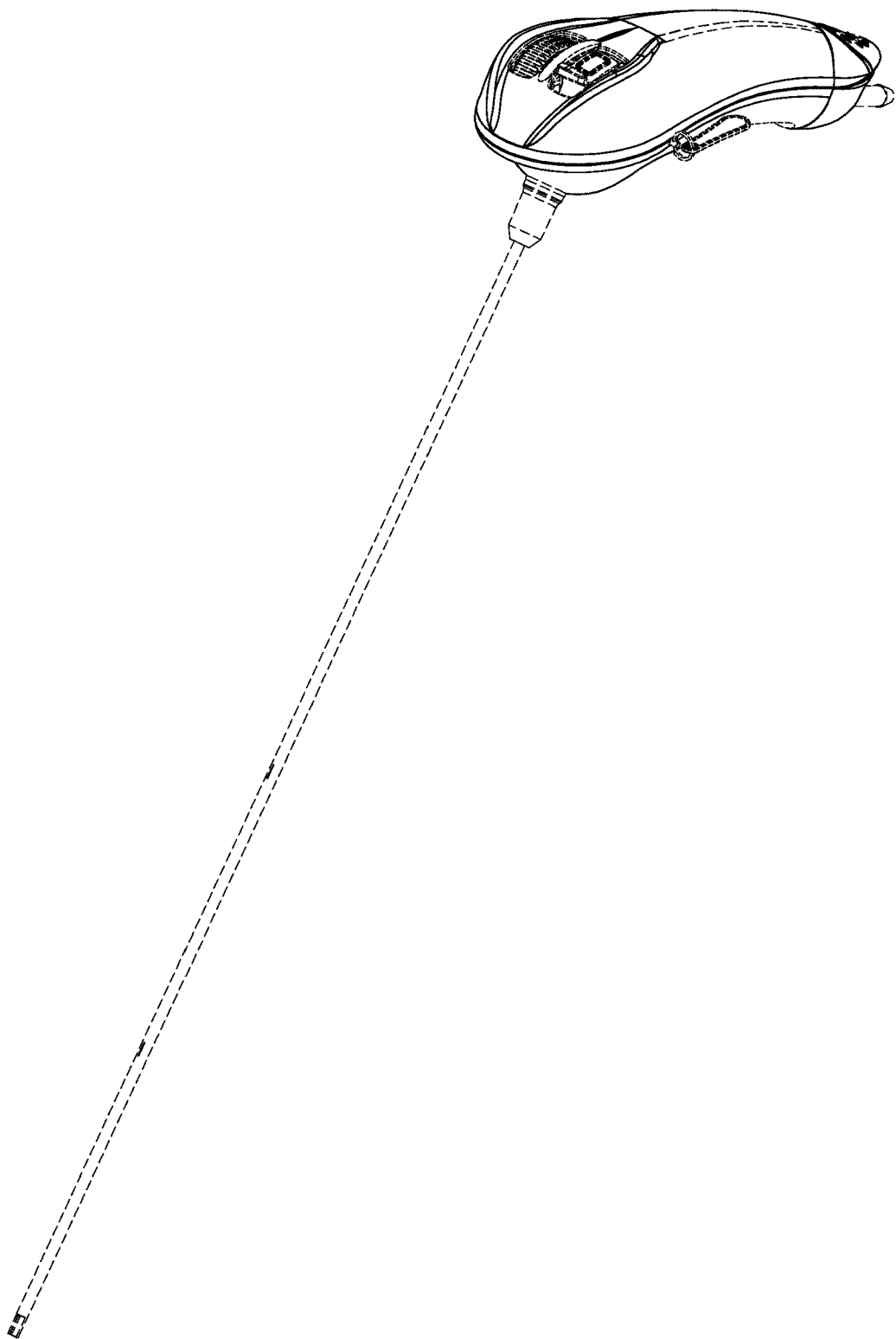
Figure 10B:
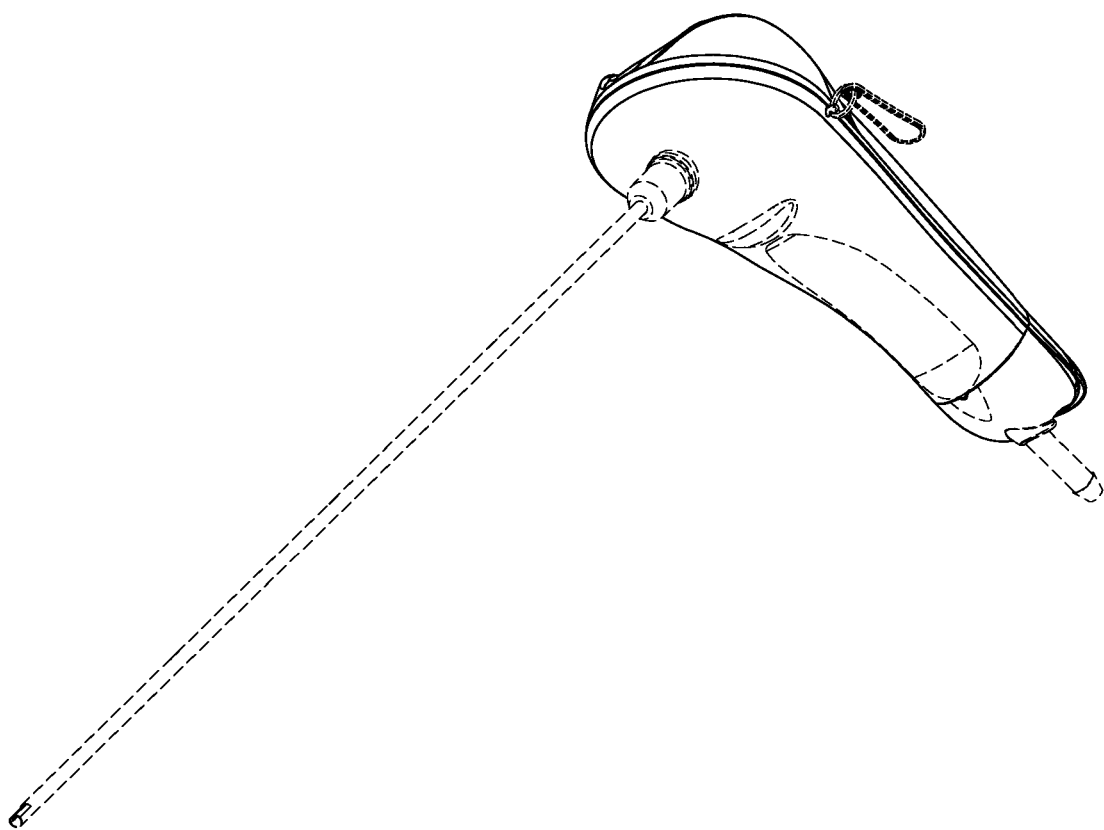
Figure 10E:
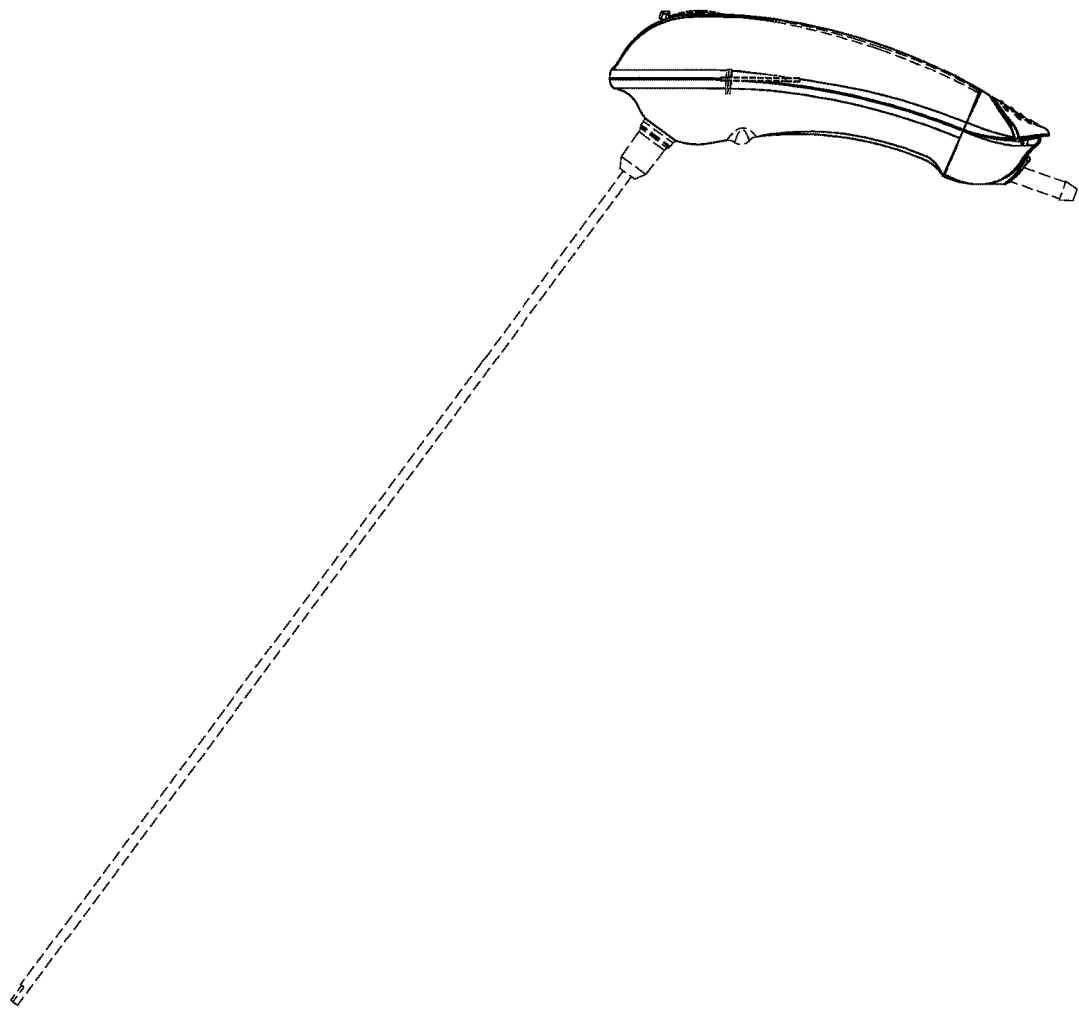
Figure 10F:
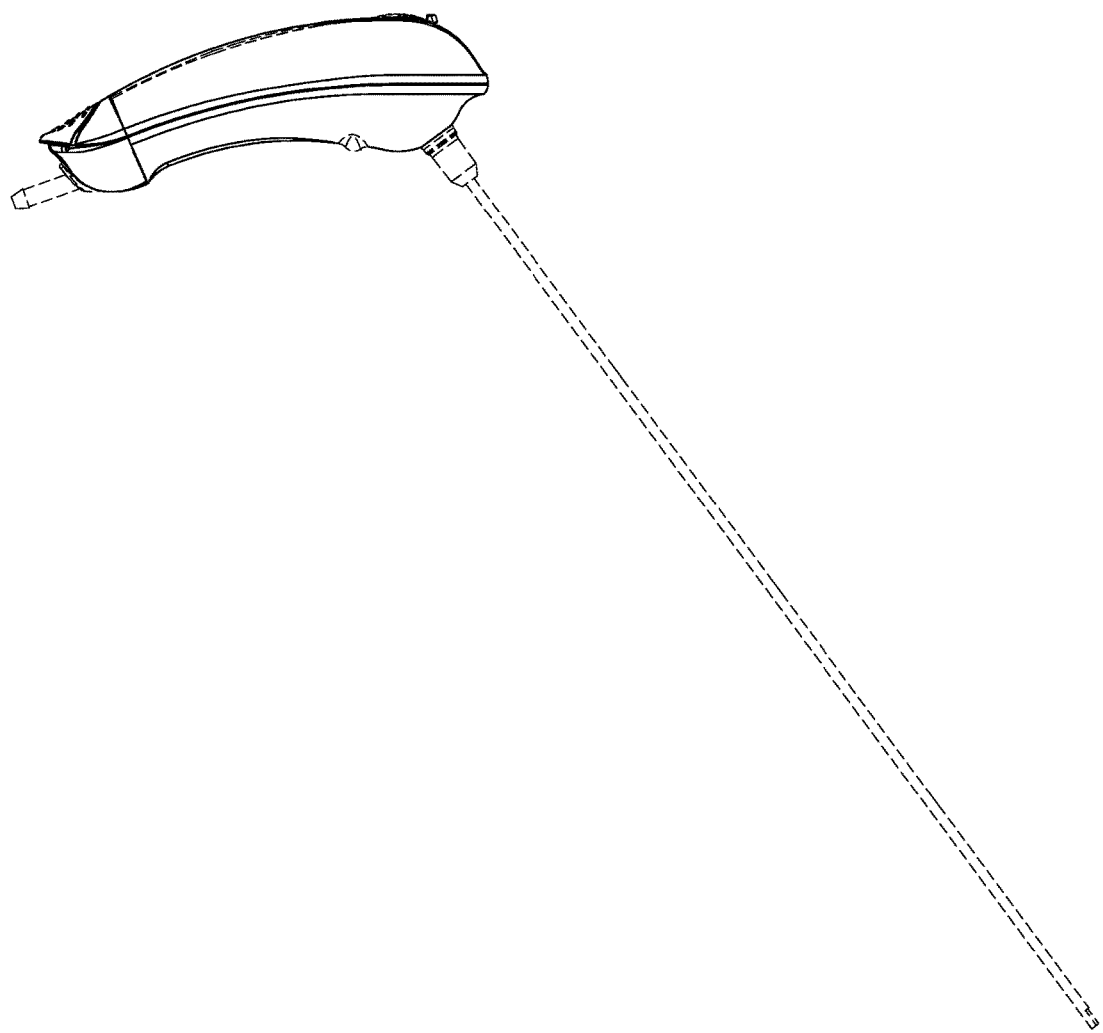

Alternatively, one or both of the rollers 114 or 116 may be made to be constructed such that they is retractable away from the plane in which it engages the optical fiber during initial advancing of the fiber through the device. A potential issue with a handpiece which is orientated at an angle with respect to the aspiration/irrigation lumen and the fiber lumen is that, with respect to the aspiration/irrigation lumen, that stones and other material can get "hung up" within that lumen in the case of sharp turns within that lumen and, with respect to the fiber lumen, the fiber gets "hung up" on its advancement into the device due to sharp turns. As can be seen by reference to FIGS. 5 through 9, however, both the silicone tube 216 seen in FIG. 9B and the tube 120 seen in FIG. 8B are gently curved which minimizes if not eliminates the "hang up" problems. This allows for the handpiece to be orientated at a more convenient angle to the lumens for the operator's use.

Turning now back to FIG. 9, the aspiration/irrigation lumen's proximal end 218, as shown may be connected by well-known means to either a source (not shown) of vacuum to allow for evacuation and aspiration of materials and fluids within the body cavity or to a source (not shown) of irrigation to allow for irrigating the body cavity. It is possible during a procedure for a stone or other material object to become lodged within the aspiration/irrigation lumen or even at the distal end of such lumen. Further vacuum may not dislodge such stone or other material. In that event, the operator may switch from a vacuum operation to an irrigation operation to force the materials lodged in the lumen to be expelled for further treatment and fragmentation.

In the operation and use of the apparatus disclosed in the present invention, a physician or other user inserts the combined optical fiber and aspiration/irrigation lumen through the urinary tract into the body cavity of the human, such as the bladder or the kidneys. After the device has been placed in the desired position, the physician or other operator inserts an optical fiber into the proximal end of the apparatus and pushes it through the metal tubes within the apparatus and through the optical fiber lumen using roller 102 until the optical fiber exits the optical fiber lumen and can be observed through a urethascope. The physician or other operator then advances the tip of the optical fiber to the stone or other materials sought to be fragmented and turns on the optical fiber activation device which may operate in high energy and long pulse mode (up to 6 joule/per pulse and up to 1700 ms per pulse) in order to reduce stone or other material repulsion and movement. Other potential parameters for the present invention include a range of about 0-6 joule/per pulse, a frequency of about 5-100 Hz, and a pulse width in the range of about 200 to about 1700 microseconds. Once a sufficient amount of material has been fragmented, the material may be withdrawn through the aspiration lumen by the physician or other operator by activating a vacuum source using switch 32. The setback of the distal tip of the fiber lumen allows the physician or other operator to observe the condition of optical fiber tip and advance the tip further to continue fragmentation of stones or other materials. Stones or other materials lodged within the aspiration/irrigation lumen may be dislodged by reversing the operation to an irrigation mode to expel the lodged material or other debris.

What is claimed is:

1. A method of fragmenting stones contained in a body lumen comprising:

providing a device for insertion into a body lumen through an endoscope, the device comprising:
a handpiece adapted to be held by an operator;
a cannula operatively associated with the handpiece;
the cannula including at least two lumens, an optical fiber lumen and an aspiration/irrigation lumen, the lumens being mounted as a unit parallel to one another along a longitudinal axis, the lumens being of a generally circular cross-section and of unequal cross-sectional size such that the circumferential wall sizes are unequal;
wherein the optical fiber lumen is of a smaller cross-sectional and circumferential size and receives an optical fiber lumen is of a smaller cross-sectional and circumferential size and receives an optical fiber with a distal fiber tip which extends through and beyond the distal tip of the optical fiber lumen and the aspiration/irrigation lumen is of a larger cross-sectional and circumferential size and provides for one or more of: (a) irrigation of the body lumen and (b) aspiration of materials from within the body lumen;
wherein the optical fiber receives and transmits a laser light through the optical fiber and out the distal end of the optical fiber, the laser light beam being utilized to fragment stones present in the body lumen during a stone fragmentation procedure; and
wherein the optical fiber lumen is formed partially within a circumferential wall of the aspiration/irrigation lumen, wherein the distal end of the circular cross-section of the optical fiber lumen terminates before the distal end of the aspiration/irrigation lumen,
wherein the optical fiber lumen continues as a half-circular shaped lumen within the circumferential all of the aspiration/irrigation lumen from the distal end of the circular cross-section of the optical fiber lumen to the distal end of the aspiration/irrigation lumen;

the method further comprising:
(a) an operator observing, through the endoscope, the optical fiber and optical fiber tip condition during the stone fragmentation procedure; and
(b) the operator advancing the optical fiber as the optical fiber tip fragments during the stone fragmentation procedure.

2. The method of claim 1, wherein the handpiece includes one or more controls to manipulate one or more of the optical fiber and to manipulate the one or more of the aspiration and irrigation of materials within the body lumen;
wherein the one or more controls to manipulate the optical fiber includes a wheel operatively associated with the handpiece which engages the optical fiber to advance the optical fiber within the handpiece;
wherein at least two rollers are operatively connected with the wheel, the at least two rollers being engageable with the optical fiber therebetween and wherein movement of the wheel causes the optical fiber to move due to contact with the moving at least two rollers;
wherein the at least two rollers are disengageable from the optical fiber such that the operator may manually advance the optical fiber;
the method further comprising, prior to steps (a) and (b):
the operator disengaging the optical fiber from the at least two rollers, then advancing the optical fiber through the optical fiber lumen until the fiber tip exits the optical fiber lumen, then engaging the optical fiber with the at least two rollers and then further advancing the optical fiber using the wheel.

3. The method of claim 2, wherein the one or more controls for one or more of aspiration and irrigation of materials includes a mechanical switch and a flexible tube operatively associated with the mechanical switch, wherein the mechanical switch, when depressed by the operator, engages and at least partially collapses the flexible tube to stop one of: aspiration or irrigation of materials in the body lumen.

* * * * *